(12) United States Patent
Kuzma et al.

(10) Patent No.: US 6,628,991 B2
(45) Date of Patent: Sep. 30, 2003

(54) MINIMALLY-INVASIVE ACCESS INTO THE COCHLEA FOR ELECTRODE INSERTION AND FLUID DELIVERY

(75) Inventors: Janusz A. Kuzma, Englewood, CO (US); Thomas J. Balkany, Coral Gables, FL (US); Thomas H. R. Lenarz, Hannover (DE)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/844,024

(22) Filed: Apr. 27, 2001

(65) Prior Publication Data

US 2003/0069613 A1 Apr. 10, 2003

Related U.S. Application Data

(60) Provisional application No. 60/201,076, filed on Apr. 28, 2000.

(51) Int. Cl.$^7$ ................................................. A61N 1/05
(52) U.S. Cl. ....................................................... 607/137
(58) Field of Search ............................ 600/379; 607/136, 607/137, 55–57

(56) References Cited

U.S. PATENT DOCUMENTS

| | | | | |
|---|---|---|---|---|
| 4,645,504 A | * | 2/1987 | Byers | 623/10 |
| 4,832,051 A | | 5/1989 | Jarvik et al. | |
| 4,892,108 A | | 1/1990 | Miller et al. | 128/784 |
| 5,545,219 A | | 8/1996 | Kuzma | 623/10 |
| 5,649,970 A | | 7/1997 | Loeb et al. | 607/57 |
| 6,074,422 A | | 6/2000 | Berrang et al. | 623/10 |
| 6,129,753 A | | 10/2000 | Kuzma | 607/137 |
| 6,149,657 A | | 11/2000 | Kuzma | 606/129 |
| 6,259,951 B1 | | 7/2001 | Kuzma et al. | 607/57 |
| 6,304,785 B1 | | 10/2001 | McCreery et al. | 607/116 |

FOREIGN PATENT DOCUMENTS

| | | |
|---|---|---|
| FR | 2622790 | 9/1987 |
| WO | 9631087 | 3/1996 |
| WO | 9906108 | 11/1999 |
| WO | 0069512 | 11/2000 |
| WO | 0069513 | 11/2000 |

* cited by examiner

Primary Examiner—Gregory R. Evanisko
(74) Attorney, Agent, or Firm—Bryant R. Gold (57) ABSTRACT

A threaded grommet, having an axial passageway therethrough, and made from a biocompatible material, such as titanium, is screwed into a cochleostomy made in the bony tissue adjacent the round window in order to provide a minimally-invasive access port into the cochlea. The threads included on the outside of the grommet engage the bony tissue and form a tight seal that holds the grommet securely in position. Such tight seal prevents cochlear fluids from escaping from inside of the cochlea. The axial passageway through the center of the grommet provides an opening, i.e., mechanical access, into the base end (the end of the cochlea nearest the round window) of the cochlea. Drugs, steroids, tissue-growth-inhibiting fluids, and the like, may be controllably delivered through the access hole into the cochlea, which access hole may be plugged when not needed. Additionally, an electrode array, e.g., a relatively short electrode array may, be inserted into the cochlea through the access hole. A preferred electrode array has from four to eight electrode contacts spaced apart along a flexible carrier. The flexible carrier is about 6–8 mm in length. The electrode contacts may be connected, in conventional manner, to suitable implantable cochlear stimulator (ICS), or equivalent pulse generator. Neither the grommet nor the short electrode array interfere with the normal hearing processes within the cochlea. Hence, both electrical stimulation and normal hearing processes may occur simultaneously within the cochlea.

9 Claims, 7 Drawing Sheets

MINIMALLY-INVASIVE ACCESS INTO THE COCHLEA FOR ELECTRODE INSERTION AND FLUID DELIVERY

The present application claims the benefit of U.S. Provisional Application Ser. No. 60/201,076, filed Apr. 28, 2000, which application is incorporated herein by reference.

BACKGROUND OF THE INVENTION

The present invention relates to implantable electrodes, and more particularly to an implantable electrode configured for minimally invasive implantation within the basal end of the scala tympani duct of a human cochlea. Such electrode may be used with a hybrid cochlear stimulator of the type described in copending patent application, Ser. No. 09/569, 696, filed May 12, 2000 (which application claims the benefit of U.S. provisional applications Ser. No. 60/134,289, filed May 14, 1999, or application Ser. No. 60/155,840, filed Sep. 24, 1999), which copending application is assigned to the same assignee as is the present application, and is incorporated herein by reference. Alternatively, such electrode may be used with any type of electrical stimulator to compensate for hearing loss in the high frequency range, and/or to provide electrical stimulation to suppress tinnitus.

Hearing loss is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

Sensorineural hearing loss, on the other hand, results due to the absence or the destruction of the hair cells in the cochlea which are needed to transduce acoustic signals into auditory nerve impulses. Persons who suffer from sensorineural hearing loss are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlea by presenting electrical stimuli directly to the ganglia of the auditory nerve located adjacent the modiolar wall of the cochlea. When triggered, the ganglia, also referred to as ganglion cells, send nerve impulses to the brain via the auditory nerve, leading to the perception of sound in the brain, and an at least partial restoration of hearing function. The common denominator in these cochlear prosthesis systems has been the implantation into the cochlea of electrodes which are responsive to a suitable external source of electrical stimuli and which are intended to transmit those stimuli to the ganglion cells, and thereby to the auditory nerve fibers.

It is estimated that a large segment of the hearing-impaired population exhibit sensorineural hearing loss relative to high frequency sounds, but maintain the ability to transduce middle-to-lower frequency sounds through functioning hair cells. For this segment of the population, there is thus a need for a "hybrid" cochlear stimulation system that electrically stimulates only the ganglion cells responsible for sensing higher frequency sounds, while allowing the normal hearing process to function for the purpose of sensing lower frequency sounds.

A cochlear prosthesis operates by direct electrical stimulation of the auditory nerve cells, bypassing the defective cochlear hair cells that normally transduce acoustic energy into electrical activity in such nerve cells. Because the ganglion cells responsible for sensing higher frequency sounds are all generally located in or near the base end of the scala tympani duct of the cochlea (the end of the scala tympani duct nearest the round window), a hybrid cochlear stimulation system thus requires at least one electrode that can be inserted into the cochlea so as to be near such cells, but so as to not block nor significantly interfere with the normal functioning of the cochlea for hair cells located deeper within the cochlea. In order not to interfere with the normal functioning of the cochlea, such electrode must be implantable or insertable into the base end of the cochlea in a minimally invasive manner, i.e., so as no to significantly interfere with the normal functioning of the round window membrane, or so as not to cause a reaction in the form of tissue or new bone formation, all of which may interfere with and adversely affect residual hearing within the implanted ear. No such electrode, or electrode system, currently exists to applicants' knowledge.

SUMMARY OF THE INVENTION

It is a feature of the present invention to provide an electrode system suitable for use with a hybrid cochlear stimulation system.

It is another feature of the invention to provide mechanical access into the cochlea without destroying or damaging the ability of the cochlea to perceive sound through the round window membrane in a natural manner. The mechanical access thus provided by the invention advantageously provides an opening through which a relatively short cochlear electrode array may be removably inserted, and/or through which drugs, steroids, or other medicinal or tissue-growth-inhibiting fluids may be readily delivered into the cochlea.

It is yet another feature of the invention to provide a cochlear electrode system that may be inserted into the cochlea in a minimally-invasive manner, and which electrode system can thereafter function without interfering with or damaging the normal operation of the round window, thereby allowing mechanical movement of the round window to set up fluid waves within the cochlea, in conventional manner.

It is an additional feature of the invention to provide a cochlear electrode system that can be inserted into the cochlea of a patient while preserving the natural hearing ability of the patient.

It is still another feature of the invention to provide a cochlear electrode system that may be removably inserted into the cochlea without causing damage to the basilar membrane.

The present invention addresses the above and other needs, and satisfies the above features, by providing a grommet that can be readily screwed into an opening made in the bony tissue adjacent the round window. Threads included on the outside of the grommet engage the bony tissue and form a tight seal that holds the grommet securely in position. Such tight seal also prevents cochlear fluids from escaping from inside of the cochlea.

The grommet further includes an access hole in its center. Such access hole provides an opening, i.e., mechanical access, into the base end of the cochlea. Fluids, e.g., drugs, steroids, tissue-growth-inhibiting fluids, and the like, may be controllably delivered through this access hole into the cochlea. Also, through this access hole, a relatively short electrode array may be inserted. Such electrode array has from four to eight, e.g., five, electrode contacts spaced apart along a flexible carrier. The flexible carrier is about 6–8 mm in length. In conventional manner, each of the electrode contacts is connected to a respective wire embedded within the carrier. The wires exit a proximal end of the carrier via a wire bundle. The wire bundle, in turn, is connectable to an implantable cochlear stimulator (ICS), or equivalent pulse generator.

Advantageously, the access hole through the grommet, while preferably round, may also be oval or oblong in shape, or otherwise keyed, to match a cross section of the carrier of the electrode array. Thus, with such shape or keying, when the electrode array is inserted through the access hole, it must assume a prescribed orientation, i.e., an orientation that positions the electrode contacts so that they must face the modiolar wall of the cochlea. Further, such prescribed orientation prevents the electrode array from twisting or turning.

The carrier of the electrode array is made from a suitable pliable substance, such as silicone rubber, or Silastic. Such pliable substance, in combination with a taper in the carrier body that provides a larger carrier cross section near a proximal tip of the electrode array than exists at a distal end of the electrode array, allows the electrode array to be tightly inserted into the access hole when fully inserted therein so as to completely close off and seal the access hole. With such a tight seal, the cochlea thus remains filled with fluid which can activate hair cells as fluid waves are established through motion of the round window membrane, which is the normal process for hearing.

In use, electrical stimulation is provided only to the base end of the cochlea through the electrode array to supplement hearing of high frequency sounds. Normal hearing processes (activation of hair cells through fluid motion) occur at the apex and middle regions of the cochlea for sensing lower frequency sounds. As needed, such normal hearing processes may be supplemented by conventional or custom hearing aid apparatus, including in-the-ear-canal or middle-ear hearing aid devices.

It is thus an object of the present invention to provide an electrode array that may be inserted into the base end of the cochlea of a hearing-impaired patient so that ganglion cells located near the base end of the cochlea may be stimulated directly with electrical stimuli, thereby enhancing the ability of the patient to sense high frequency sounds.

It is a further object of the invention to provide an electrode array suitable for insertion into the base end of the scala tympani duct of a human cochlea without destroying the function of the basal membrane (the basal membrane separates the scala tympani from the scala vestibule, another one of the ducts within the cochlea), and without causing fluid to escape from the scala tympani, or other ducts of the cochlea, thereby allowing normal hearing processes (fluid motion activation of hair cells) to continue to occur in the cochlea simultaneously with electrical stimulation.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components or elements throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
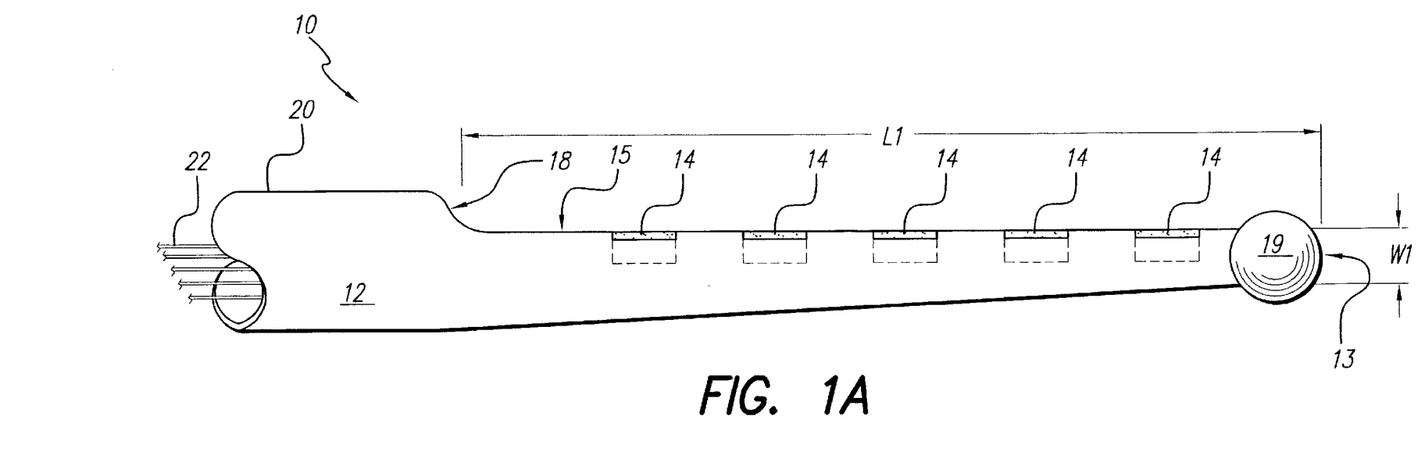
FIGS. 1A and 1B show a side and top view, respectively, of a short electrode array that may be used with the present invention.
Figure 1B:
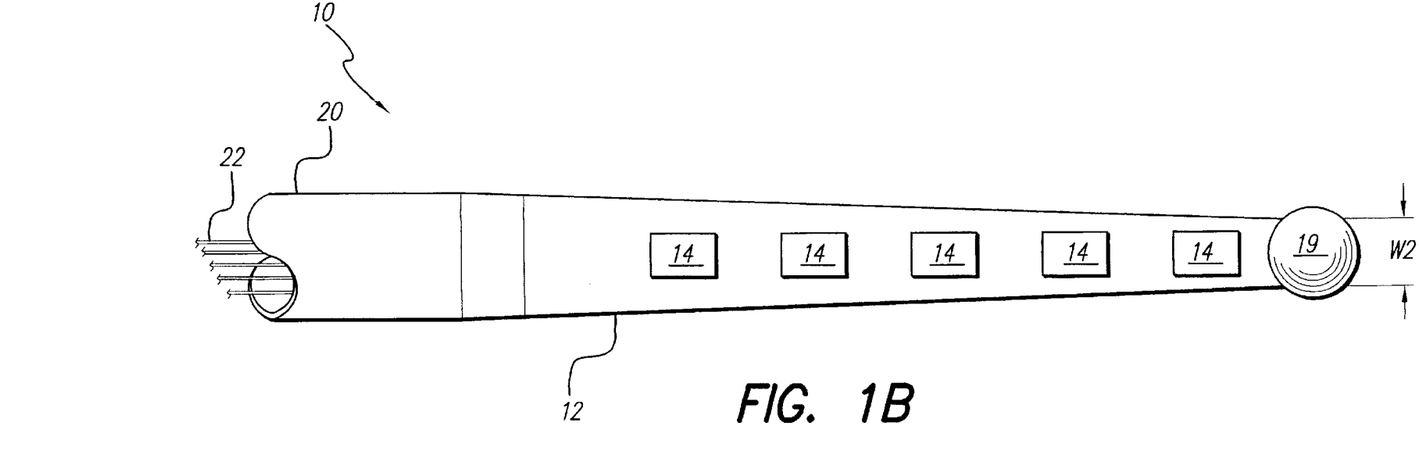

An electrode array 10 suitable for use with the present invention is illustrated in FIGS. 1A and 1B. FIG. 1A is a side view of the electrode array 10; and FIG. 1B is a view of a medial side of the electrode array 10. (Thus, for purposes of the present application, the "medial side" of the electrode array 10 is the side on which a plurality of spaced-apart electrode contacts 14 are located.)

As seen in FIGS. 1A and 1B, the electrode array 10 includes a plurality of spaced-apart electrode contacts 14 on a flexible carrier 12. In the preferred embodiment, each of the electrode contacts 14 resides on the same side—the medial side 15—of the carrier 12. Each electrode contact 14 has at least one wire conductor 22 connected thereto. These wire conductors are embedded within the flexible carrier 12 and exit through a proximal end of the carrier 12 within a flexible cable 20. The cable 20, including its wire conductors 22, connect to a pulse generator, or other suitable stimulator (not shown). Such wire conductors 22 thus provide a means for making electrical contact with each of the electrode contacts 14. When used as part of a hybrid or other cochlear stimulator system, the pulse generator, or other stimulator, thus generates electrical pulses or electrical currents ("electrical stimuli") that is/are applied to selective ones of the electrode contacts 14 in order to evoke a desired response from the ganglion cells located in the vicinity of the electrode contacts 14.

At a proximal end of the electrode array 10 is a shoulder 18. The shoulder 18 comprises a portion of the flexible carrier 12 that extends outwardly (or upwardly, as seen in FIG. 1A) from the medial surface 15 on which the electrode contacts 14 are located. The shoulder 18 thus defines a boundary between the electrode array and the lead 20 which connects the electrode array to a suitable pulse generator.

Typically, the electrode array 10 is somewhat thinner in one direction than in the other. Stated differently, the electrode array 10 is flattened in one direction, and if viewed in cross section, would resemble a rectangle having unequal sides. For example, with the electrode contacts 14 facing upwards, as shown in FIG. 1A, the width of the carrier body 12, excluding the ball 19 at the distal end of the array, is a distance W1. As seen in FIG. 1B, with the electrode contacts 14 facing out of the plane of the paper, the width of the carrier body 14 is W2. W2 may be 1.1 to 3 times larger than W1. Typically, W1 may be about 0.5 to 1.0 mm; whereas W2 may be on the order of 1.5–2 mm.

The length of the electrode array 10, from the shoulder 18 to a distal tip 13 is a distance L1. This distance L1 will typically be 6–8 mm. The number of spaced-apart electrode contacts 14 positioned on the medial side of the carrier body 14 may vary from four to eight. For the example shown in FIGS. 1A and 1B, there are five electrode contacts 14.

As seen in FIGS. 1A and 1B, the electrode contacts 14 are all on a medial side of the electrode array, i.e., are all on the same side of the carrier 12, and the medial side is usually the only "flat" side of the carrier 12 (although in some embodiments, there may be more than one "flat" side of the carrier). Such positioning is preferred because when inserted into the cochlea, this medial side of the electrode array 10 is positioned so as to face the modiolar wall of the cochlea, where the ganglion cells are located. Thus, such positioning places the electrode contacts closer to the modiolar wall, and thereby allows electrical stimulation of the ganglion cells to occur more efficiently (i.e., with less power). However, it should be noted that such positioning of the electrode contacts 14 is not mandatory. In practice, the electrode contacts 14 could be located on any side of the flexible carrier body 12, or on all sides (e.g., bands or rings), and the electrode array could still perform its intended function of stimulating the ganglion cells located near the base end of the cochlea.

While any suitable technique may be used to make the electrode array 10, a preferred manner of making an electrode array 10 having all of its electrode contacts on a medial side of the carrier, and having individual wires connected to each of the electrode contacts, is disclosed in U.S. Pat. No. 6,129,753, which patent is incorporated herein by reference.

Figure 2A:
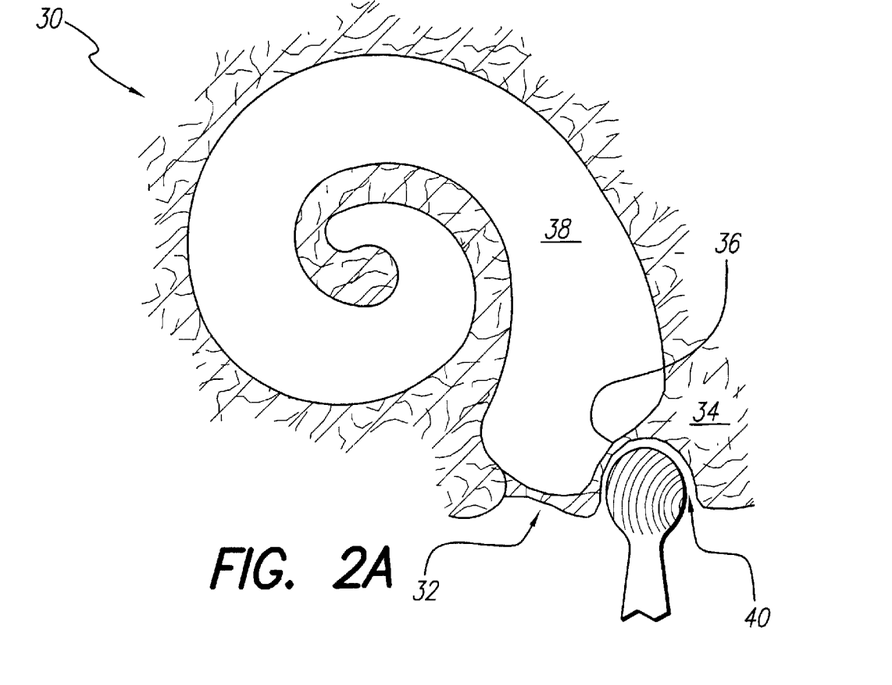
FIG. 2A illustrates a first step of drilling a cochleostomy about 1 mm to the side of the round window, but without penetrating the spiral ligament.
Figure 2B:
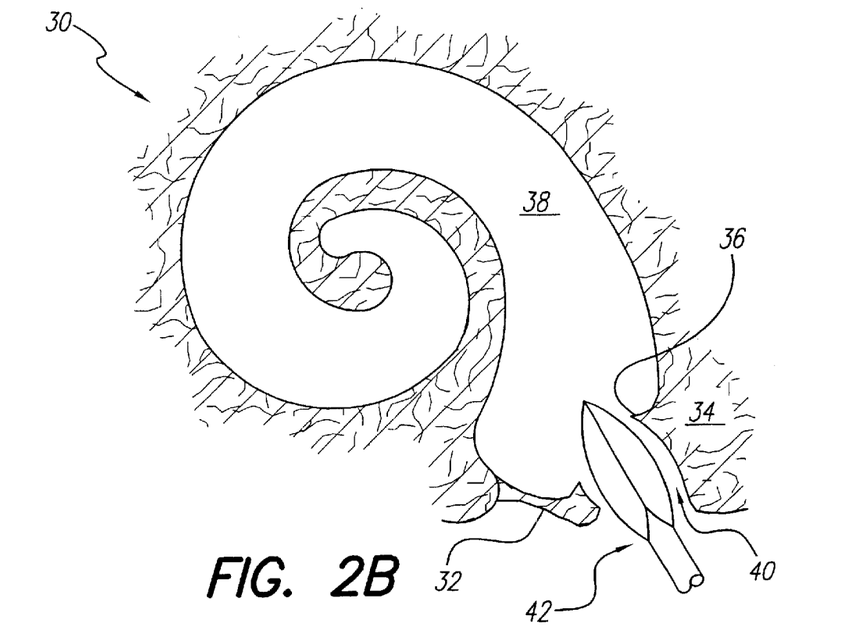
FIG. 2B illustrates a second step of using a micro-spear and/or micro-pick to remove the spiral ligament membrane from the cochleostomy.

Next, with reference to FIGS. 2A and 2B, the preferred process for making a cochleostomy for use by the grommet of the present invention is illustrated. FIG. 2A illustrates the spiraling scala tympani duct 38 of a cochlea 30. The round window 32 separates the space within the cochlea, which is normally filled with a fluid, from the middle ear. The cochlea, especially the base region of the cochlea in the vicinity of the round window 32 is surrounded by bony tissue 34. As seen in FIG. 2A, a first step for making a suitable cochleostomy is to drill a hole 40, about 1.0 mm in diameter, on a lateral side of the round window 32. A preferred location for the drilled hole 40 is about 1 mm from the closest edge of the round window 32. The hole 40 is drilled as deep as possible without penetrating the spiral ligament membrane 36. Then, as seen in FIG. 2B, a micro-spear 42, and/or micro-pick, is used to remove the spiral ligament membrane 36 from the hole 40.

Figure 3:
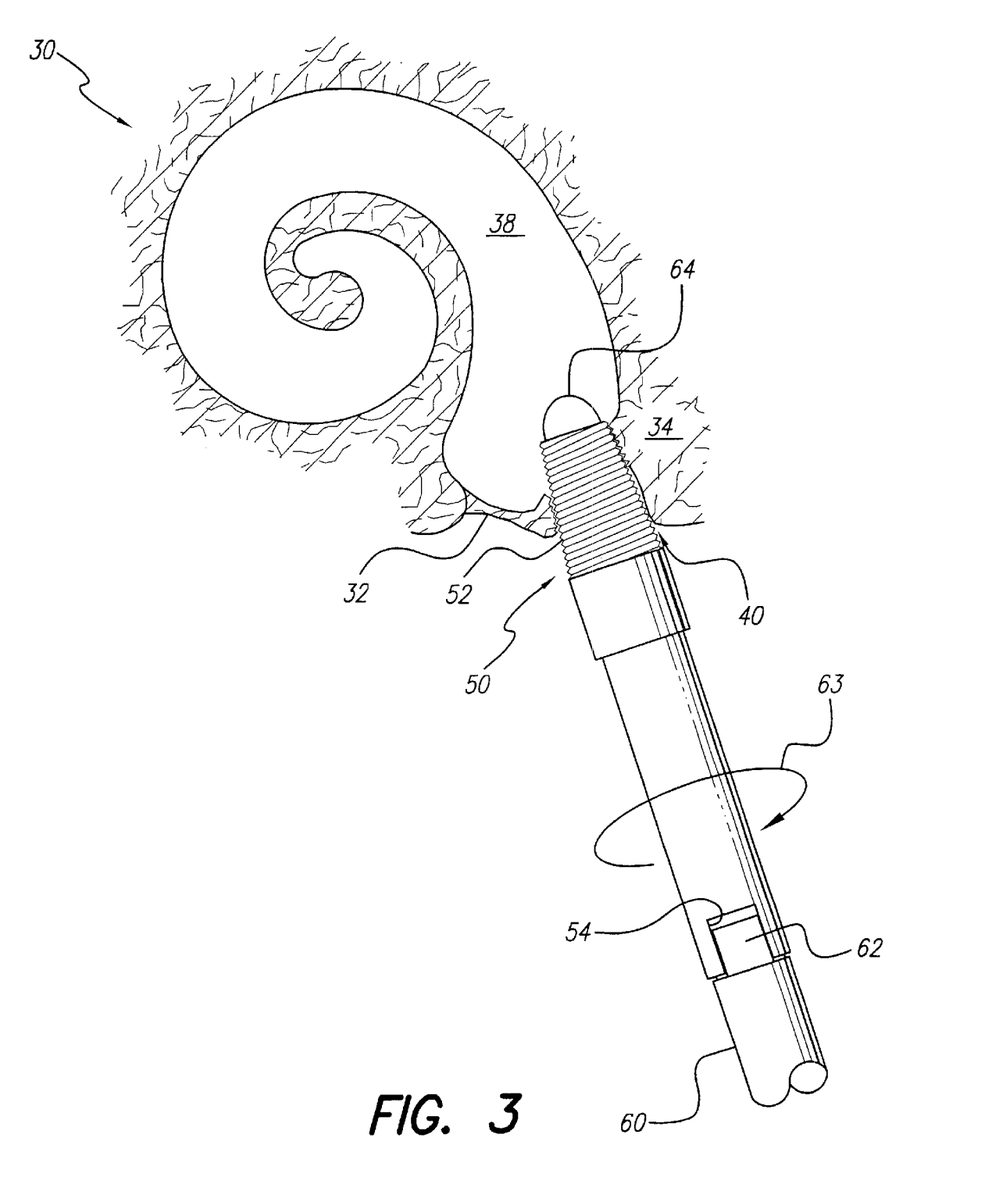
FIG. 3 shows screwing the threaded grommet of the present invention into the cochleostomy.

Once the hole 40 has been drilled and micro-speared/micro-picked, as required in order to remove the spiral ligament membrane 36, a titanium grommet 50 is screwed into the hole 40 with the aid of a special driver tool 60, as seen in FIG. 3. The grommet-insertion tool 60 has a centering rod 64 that protrudes from its distal end. This centering rod 64 has a length sufficient to allow it to pass all the way through an axial access hole 56 (shown in FIG. 4) through the center of the grommet 50. At a proximal end of the grommet 50 is an engaging slot 54. The tool 60 has a corresponding blade 62 adapted to be received within the slot 54. Once the blade 62 is seated within the slot 54, the driver tool 60 may be rotated in a clockwise direction, as shown by the arrow 63, in order to screw grommet into the cochleostomy hole 40 previously made in the bony tissue 34.

As seen in FIG. 3, the grommet 50 has a treaded distal portion that is conically shaped. The narrowest part of the conically-shaped distal portion 58 (see FIG. 6A) is the most distal portion. Threads 52 are etched on the outer surface of the conically-shaped distal portion of the grommet that tend to drive the grommet deeper into the hole 40 as the grommet is rotated clockwise. Thus, as the grommet is rotated clockwise by the tool 60, the grommet embeds itself firmer and firmer into the bony tissue 34, until it is securely seated in, and seals, the hole 40.

Once the grommet 50 is threadably secured and sealed within the cochleostomy hole 40, the tool 60 is removed therefrom by simply retracting the tool, including its centering rod 64, back through the axial hole 56 in the center of the grommet.

If needed or desired, a suitable wetting agent and/or sealant may be placed on the threads of the grommet 50 during the process of rotatably driving the grommet deeper and deeper within the cochleostomy hole 40, much like plumber's putty is placed on the threads of one pipe being screwed into another, thereby providing a tight secure seal between the bony tissue 34 and the threads 52.

Figure 4:
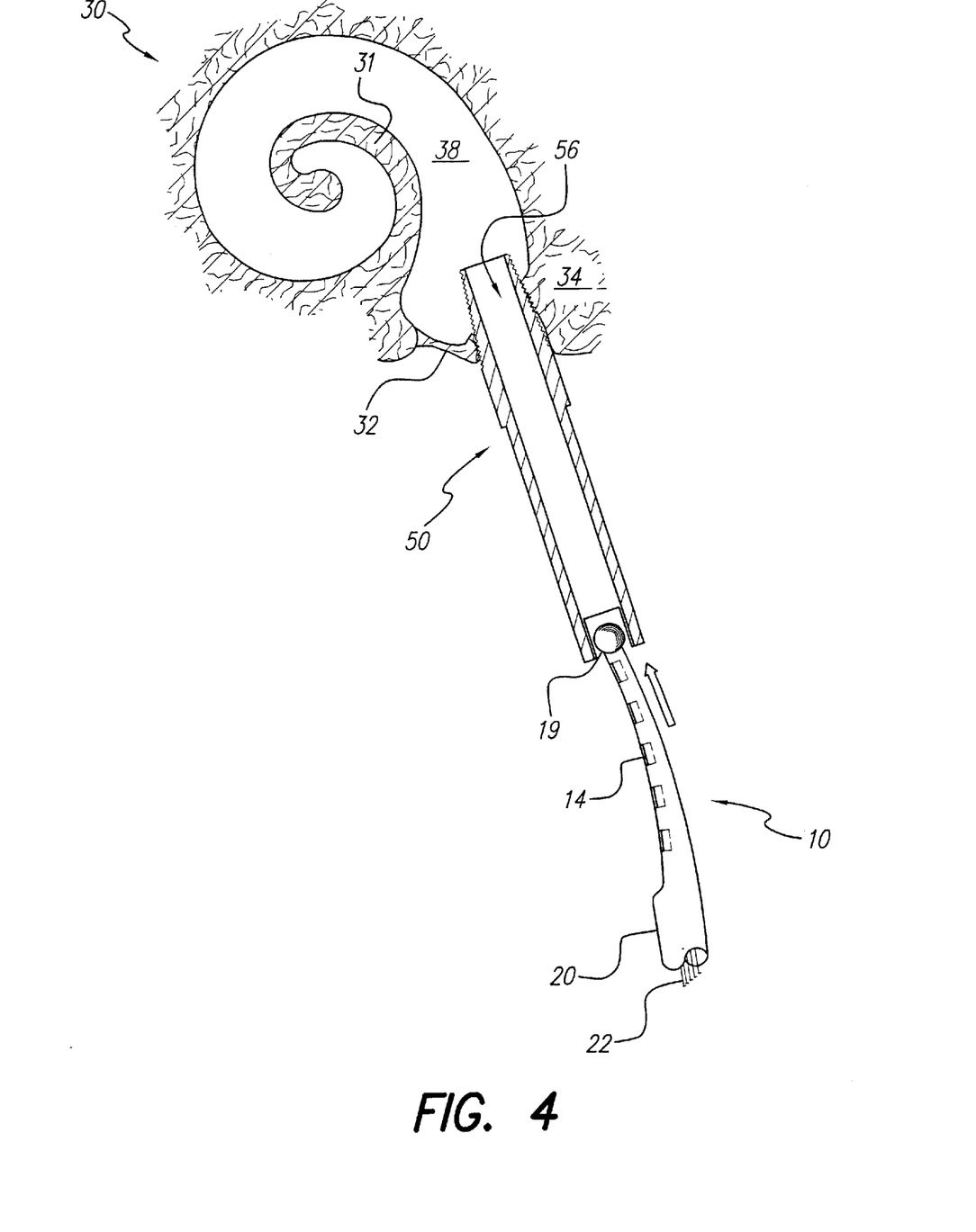
FIG. 4 depicts insertion of the electrode array into the base end of the cochlea through the access hole in the center of the grommet.

With the grommet firmly screwed into the bony tissue through which the cochleostomy is made, an access hole 56 is thus provided into the inside portion 38 of the cochlea 30, as seen best in FIG. 4. This access hole 56 may be used for several purposes, including the delivery of desired or needed drugs, steroids, fluids, or tissue-growth-inhibiting substances to the inside of the cochlea. When not needed, the access hole 56 may be plugged to prevent fluids within the cochlea from escaping.

A primary purpose of the access hole 56 is to allow the electrode array 10 to be easily inserted into the cochlea 30, as shown in FIG. 4. That is, with the grommet 50 in place within the cochleostomy, it is a relatively simple matter for the electrode array 10 to be slid through the axial hole 56 that passes through the center of the grommet 50, with the electrode array itself serving as the plug that prevents cochlea fluids from escaping from the cochlea. O-rings, or equivalent sealing mechanisms, placed either on the inside of the access hole and/or on the outside of the electrode array, may be utilized to enhance the seal that is made by the electrode or other plug that is placed in the access hole.

Figure 5:
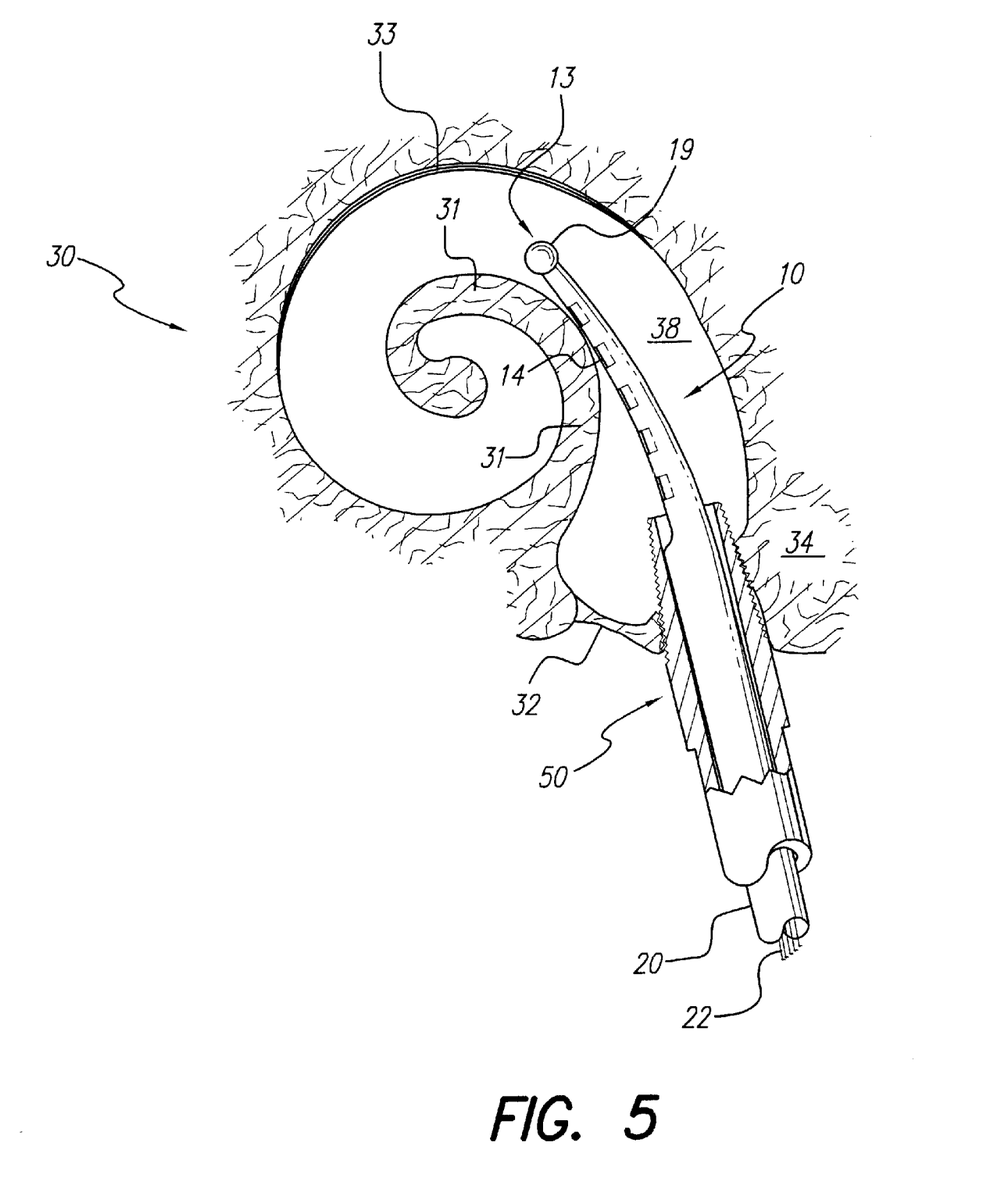
FIG. 5 illustrates the position of the electrode array within the cochlea when fully inserted through the access hole of the grommet, and further shows the manner in which the electrode array seals the access hole.

As the electrode array is inserted through the access hole, it is oriented so that the electrode contacts 14 face the modiolar wall 31 of the cochlea. Eventually, the array 10 reaches the position where it is fully inserted within the grommet 50, as shown in FIG. 5. In its fully inserted position, the electrode contacts 14 are advantageously facing, and in close proximity to, the modiolar wall 31, thereby allowing stimulation of the ganglion cells located within the modiolar wall to occur more efficiently, i.e., using less power.

Further, in its fully inserted position, the distal tip 13 of the electrode array 10 should not be in contact with the delicate basal membrane 33, thereby preventing damage to the basal membrane. As a further precaution, a soft ball 19 is formed at the distal tip of the array 10, thereby helping prevent damage to surrounding tissue should the distal tip 13 inadvertently come in contact with the basal membrane 33 or other delicate tissue. (Note: the heavy line 33 shown in FIG. 5 to represent the basal membrane is not exactly anatomically correct. The basal membrane separates the scala tympani 38 from the other ducts within the cochlea, and as such, the basal membrane is more above the scala tympani 38 as shown in FIG. 5 than at one side of it, as suggested by the heavy line 33. However, because all of the channels within the cochlea are more or less parallel to each other, and all spiral together, it is common for an electrode inserted into the cochlea to engage the basal membrane, particularly at the first turn of the scala tympani, because the electrode must not only bend to go around the turn, but it must also bend upwards to follow the spiral. The electrode array 10 used with the grommet 50 of the present invention, however, is designed to be sufficiently short so as not to reach the first bend or turn of the scala tympani within the cochlea.)

It is significant that, with the array 10 fully inserted into the cochlea 30, as shown in FIG. 5, the operation of the round window 32 is not impaired. Thus, the normal hearing processes of the inner ear, e.g., establishing fluid waves or motion within the cochlea that triggers hair cells, may occur at the same time that electrical stimulation is provided through the electrode array 10.

Figure 6A:
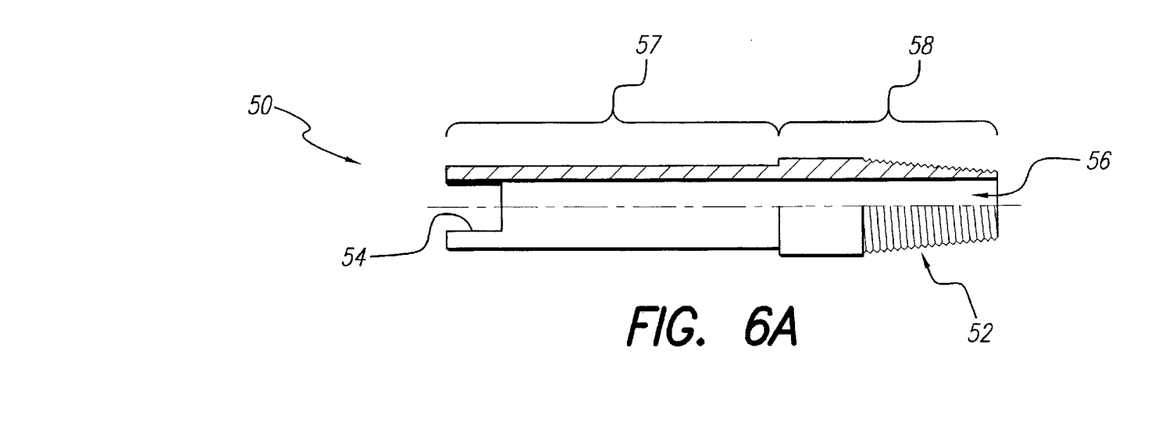
FIG. 6A shows a side view of the grommet, with a portion of the grommet cutaway.
Figure 6B:
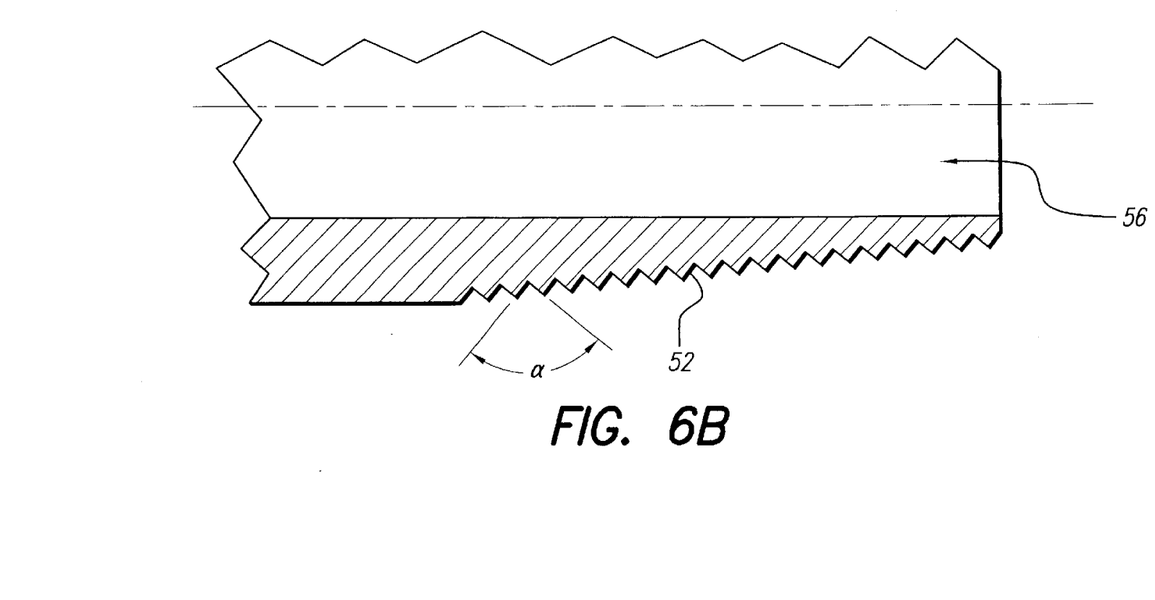
FIG. 6B shows details associated with the threads on the outer surface of the grommet.

Next, with reference to FIGS. 6A and 6B, additional details relative to the one embodiment of the grommet 50 are illustrated. As seen in FIG. 6A, the grommet 50 has a conically-shaped distal portion 58 that is threaded with threads 52. The narrowest part of the conically-shaped distal portion 58, at the distal tip of the grommet, is about 1 mm. The widest part of the conically-shaped distal portion 58 is about 1.4 mm. The length of the conically-shaped distal portion 58 is about 3.2 mm, of which about 2 mm are threaded.

A shaft portion 57 of the grommet 50 extends proximally from the conically-shaped distal portion 58. For the embodiment shown in FIG. 6A, the length of the shaft portion 57 is about 4.8 mm, making the overall length of the grommet 50, i.e., the sum of the shaft portion 57 and the conically-shaped distal portion 58, about 8.0 mm. The diameter of the shaft portion is about 1.2 mm.

A slot 54 is formed at the proximal end of the shaft portion 57. The slot 54 as a depth of about 0.8 mm, and a width of about 0.7 mm.

An access hole 56 (or access channel) passes through the center of the grommet 50. For the embodiment shown in FIG. 6A, the access hole 56 has a diameter of about 0.8 mm.

Details associated with the threads in the conically-shaped distal portion 58 are depicted in FIG. 6B. Threads 52 are formed in the tapered portion of the conically-shaped distal portion 56 and are spiraled so as to allow clockwise rotation of the grommet drive the grommet deeper into the cochleostomy. The threads 52 preferably are cut at an angle α of about 90°, as illustrated in FIG. 6B. That is, as seen in FIG. 6B, the angle α formed at the bottom of each thread is approximately 90°. The depth of the threads 52 is about 0.05 mm.

The grommet 50 is made from a suitable biocompatible metal, such as titanium (≧95%) or a high grade stainless steel. A preferred material is titanium. Ceramic or other similar substances could also be used, if adequate machining and/or molding processes are available for making the grommet. For the relatively small size of the grommet 50, however, present tooling techniques and machining practices suggest that the grommet 50 be made from a metal, such as titanium.

It is to be emphasized that the particular size and form of the grommet 50 illustrated in FIGS. 6A and 6B is only exemplary. Variations to the size and form may be made by those of skill in the art, as needed. In particular, the length of the shaft portion 57, the amount of taper in the conically-shaped distal portion 58, the size and angle of the cut of the threads 52, the size of the slot 54, and the size of the access hole 56, are all parameters that may be modified, as required, in order to allow the grommet 50 to better perform its intended function.

Figure 7A:
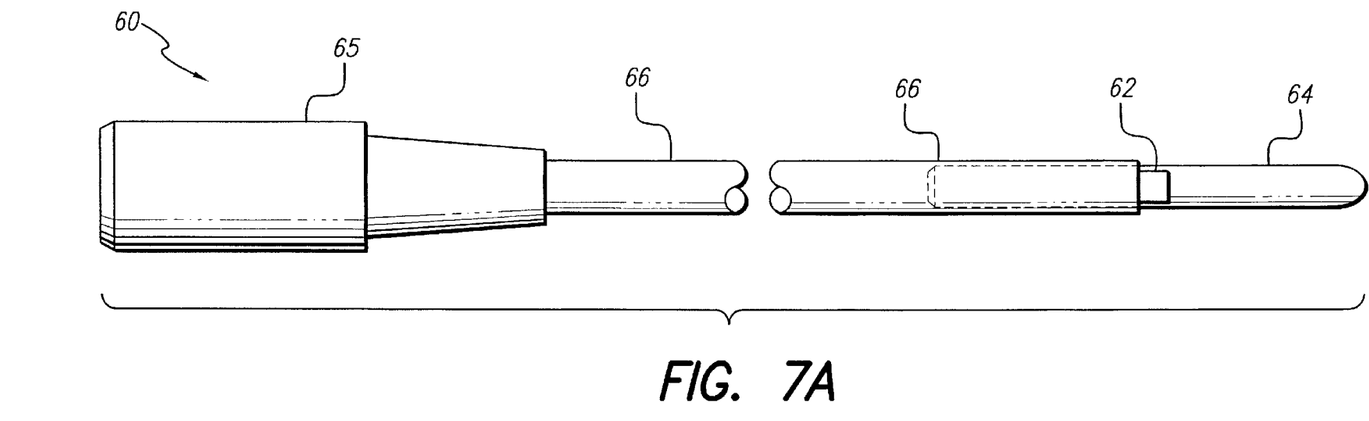
FIG. 7A illustrates a side view of a screw-driver tool that may be used to screw the grommet into the cochleostomy.
Figure 7B:
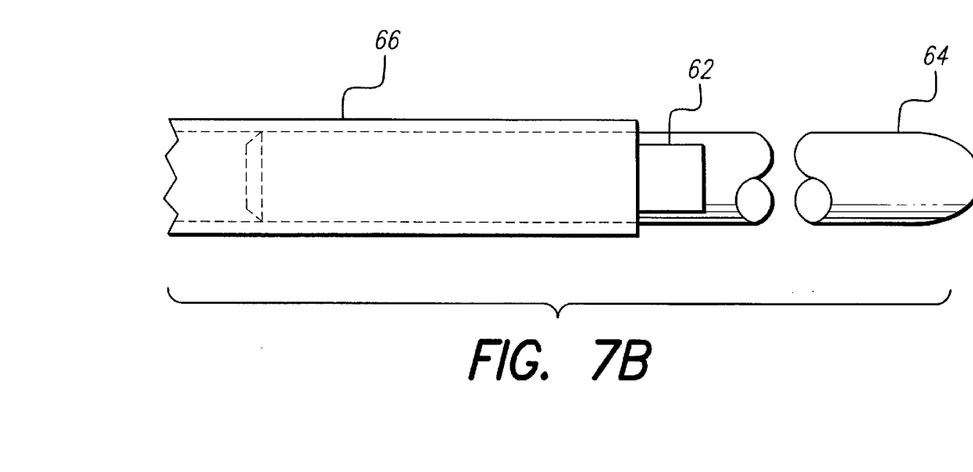
FIG. 7B is an enlarged view of the tip of the tool shown in FIG. 7A.
Figure 7C:
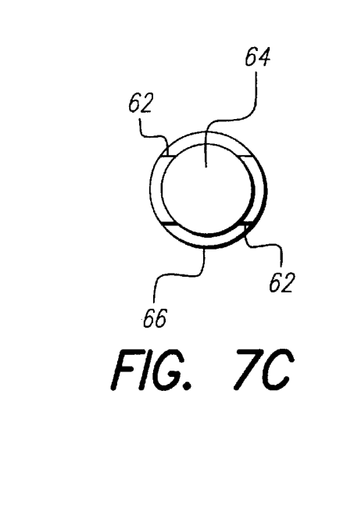
FIG. 7C is an end view of just the tip portion of the tool of FIG. 7A.

Turning next to FIGS. 7A, 7B and 7C, additional details associated with the driver tool 60 are illustrated. FIG. 7A depicts a side view of the tool 60. As seen in FIG. 7A, the tool 60 includes a shaft portion 66 at the distal end of which is a blade 62. Preferably, at least the distal end of the shaft portion 66 is hollow so as to allow a proximal end of a centering rod 64 to be inserted into the shaft 66, while a distal end of the centering rod 64 extends out from the distal end of the shaft 66 a prescribed distance, e.g., 9 mm. The protruding centering rod 64 thus allows the grommet 50 to be slid onto the rod 64 prior to guiding the grommet into the cochleostomy. Hence, the centering rod 64 holds the grommet in place on the distal end of the tool 60 as the grommet is guided for insertion into the cochleostomy.

In a preferred embodiment, the shaft portion 66 of the tool 60 is made from the same material as is a 16 gauge I.V. catheter needle. The length of the shaft 66 is about 60 mm. A handle 65 is affixed to the proximal end of the shaft portion 66 in order to allow the tool 60 to be easily rotated with one hand, like a screwdriver.

The blade 62 is formed at the distal tip of the shaft portion 66, as seen best in FIG. 7B. Because the centering rod 64 extends out from the distal end of the shaft portion 66, the blade 62 is bifurcated into two parts, one part on each side of the centering rod 64, as seen best in FIG. 7C. For the embodiment shown in FIGS. 7A, 7B and 7C, the blade 62 is about 0.7 mm in length and width.

The particular embodiment of the tool 60 shown in FIGS. 7A, 7B and 7C is only exemplary. Variations in the dimensions illustrated may be made in order to best suit the needs of the particular application, and in order to better allow the tool 60 to perform its intended function of driving (turning) the grommet 50 as it is inserted into the cochleostomy.

As described above, it is thus seen that the present invention provides an electrode system suitable for use with a hybrid cochlear stimulation system, e.g., a stimulation system that provides electrical stimulation of the ganglion cells located near the base of the cochlea, which cells are responsible for hearing higher frequency sounds, while allowing the normal hearing processes occur for hearing lower frequency sounds.

It is further seen that invention provides mechanical access into the cochlea without destroying or damaging the ability of the cochlea to perceive sound through the round window membrane in a natural manner. The mechanical access thus provided advantageously provides an opening through which a relatively short cochlear electrode array may be removably inserted, and/or through which drugs, steroids, or other fluids or tissue-growth-inhibiting substances may be readily delivered into the cochlea.

It is also seen that the invention provides a cochlear electrode system that may be inserted into the cochlea in a minimally-invasive manner, and which electrode system may thereafter function without interfering with or damaging the normal operation of the round window, thereby allowing mechanical movement of the round window to set up fluid waves within the cochlea, in conventional manner. Thus, it is seen that the invention allows a cochlear electrode system to be used that preserves the natural hearing ability of the patient; and which allows a cochlear electrode system to be removably inserted into the cochlea without causing damage to the basilar membrane or other delicate parts of the inner ear.

While the invention herein disclosed has been described by means of specific embodiments and applications thereof, numerous modifications and variations could be made thereto by those skilled in the art without departing from the scope of the invention set forth in the claims.

What is claimed is:

1. A minimally-invasive electrode system for providing electrical stimulation to ganglion cells responsible for sensing higher frequency sounds, the electrode system comprising:

a grommet adapted for insertion into a cochleostomy formed in bony tissue adjacent the round window, the grommet having an axial passageway through the center thereof;

an electrode array insertable through the axial passageway of the grommet, wherein the electrode array has a cross-sectional size that allows the array to snugly engage and fill the axial passageway when inserted to a prescribed depth, wherein fluids may not pass through the axial passageway when the electrode array is inserted in the axial passageway to the prescribed depth;

wherein the electrode array comprises a flexible carrier on which a multiplicity of spaced-apart electrode contacts are carried and in which a multiplicity of wires are embedded, wherein each electrode contact has at least one of the multiplicity of wires connected thereto; and wherein the portion of the electrode array that is insertable through the axial passageway of the grommet is no longer than about 8 mm.

2. The electrode system of claim 1 wherein the grommet comprises a conically-shaped member having threads on an outer surface thereof, and a slot on a back side thereof; and wherein a rotational driving force applied to the slot on the back side of the grommet causes the grommet to be screwed into bony tissue surrounding the cochleostomy.

3. The electrode system of claim 2 further including a driving tool having a blade adapted to engage the slot on the back side of the grommet in order to facilitate applying the rotational driving force to the grommet.

4. The electrode system of claim 3 wherein the driving tool further includes a distally protruding centering rod, wherein the centering rod is insertable through the axial passageway of the grommet in order to hold the grommet on the distal end of the driving tool as the grommet is guided into the cochleostomy and a rotational driving force is applied to the slot on the back side of the grommet.

5. The electrode system of claim 1 wherein the electrode array has no more than five spaced-apart electrode contacts thereon.

6. The electrode system of claim 5 wherein the spaced-apart electrode contacts are all located on one side of the flexible carrier.

7. The electrode system of claim 6 wherein the one side of the flexible carrier on which all of the spaced-apart electrode contacts are located is flat.

8. The electrode system of claim 7 wherein the axial passageway through the center of the grommet is keyed so that when the electrode array is inserted therethrough, the flat side of the flexible carrier and the electrode contacts face in the same direction.

9. The electrode system of claim 1 wherein the electrode array has a ball formed on the array distal tip, the ball having a diameter that allows the ball to just fit through the axial passageway of the grommet.

* * * * *

UNITED STATES PATENT AND TRADEMARK OFFICE
CERTIFICATE OF CORRECTION

PATENT NO.    : 6,628,991 B2
DATED         : September 30, 2003
INVENTOR(S)   : Kuzma et al.

It is certified that error appears in the above-identified patent and that said Letters Patent is hereby corrected as shown below:

<u>Title page,</u>
Item [*] Notice: Subject to any disclaimer, the term of this patent is extended or adjusted under 35 USC 154(b) by (0) days
Delete the phrase "by 0 days" and insert -- by 257 days --

Signed and Sealed this

Twenty-fifth Day of November, 2003

JAMES E. ROGAN
*Director of the United States Patent and Trademark Office*